(12) United States Patent
Lee et al.

(10) Patent No.: US 11,688,187 B1
(45) Date of Patent: Jun. 27, 2023

(54) SYSTEM AND METHOD FOR MEASURING DISH SIZE AND PROVIDING NUTRITION INFORMATION USING IMAGE RECOGNITION AND AUGMENTED REALITY BASED ON ARTIFICIAL INTELLIGENCE

(71) Applicant: doinglab Corp., Seoul (KR)

(72) Inventors: Hyun Suk Lee, Hwaseong-si (KR); Song Baik Jin, Seoul (KR); Dae Han Kim, Seoul (KR); Chae Yoon Han, Seoul (KR)

(73) Assignee: doinglab Corp., Seoul (KR)

( * ) Notice: Subject to any disclaimer, the term of this patent is extended or adjusted under 35 U.S.C. 154(b) by 0 days.

(21) Appl. No.: 18/161,614

(22) Filed: Jan. 30, 2023

(30) Foreign Application Priority Data

Aug. 25, 2022 (KR) .................. 10-2022-0106815

(51) Int. Cl.
*G06V 20/68* (2022.01)
*G06T 11/00* (2006.01)
(Continued)

(52) U.S. Cl.
CPC .............. *G06V 20/68* (2022.01); *G06T 7/62* (2017.01); *G06T 11/00* (2013.01); *G06V 10/26* (2022.01);
(Continued)

(58) Field of Classification Search
CPC ........ G06V 20/68; G06V 20/20; G06V 10/26; G06V 10/774; G06V 10/764; G06T 7/62; G06T 11/00; G16H 20/60
See application file for complete search history.

(56) References Cited

U.S. PATENT DOCUMENTS

| | | | |
|---|---|---|---|
| 2012/0031805 A1* | 2/2012 | Stolarczyk | A47J 39/006 206/541 |
| 2020/0159750 A1* | 5/2020 | Shadrokh | G06V 10/50 |

FOREIGN PATENT DOCUMENTS

| | | | | |
|---|---|---|---|---|
| KR | 10-0824350 B1 | | 4/2008 | |
| KR | 100824350 B1 | * | 4/2008 | ............. G06Q 50/22 |

(Continued)

OTHER PUBLICATIONS

Notice of Preliminary Examination Result issued in KR 10-2022-0106815; mailed by the Korean Intellectual Property Office dated Sep. 16, 2022.

*Primary Examiner* — Reza Aghevli
(74) *Attorney, Agent, or Firm* — Studebaker & Brackett PC

(57) ABSTRACT

Disclosed are a system and a method for measuring dish size and providing nutritional information using image recognition and augmented reality based on artificial intelligence. The system includes: at least one imaging device acquiring at least one image including at least one dish or at least one food contained in each dish; a service providing apparatus for detecting the at least one dish and the at least one food from the at least one image when the at least one image is received, confirming the name of each detected food on the basis of a learning model, predicting the size of each detected dish, predicting the volume of each detected food using the predicted size of the dish, and generating nutritional information using the predicted volume of each food and pre-stored food information; and a user terminal for visualizing and displaying the nutritional information when the nutritional information is received.

10 Claims, 14 Drawing Sheets

(51) Int. Cl.
*G06V 20/20* (2022.01)
*G16H 20/60* (2018.01)
*G06V 10/26* (2022.01)
*G06V 10/764* (2022.01)
*G06V 10/774* (2022.01)
*G06T 7/62* (2017.01)

(52) U.S. Cl.
CPC .......... *G06V 10/764* (2022.01); *G06V 10/774* (2022.01); *G06V 20/20* (2022.01); *G16H 20/60* (2018.01)

(56) References Cited

FOREIGN PATENT DOCUMENTS

| KR | 20180116779 A | * | 4/2008 | ............ G06Q 50/22 |
|----|---------------|---|--------|-------------------------|
| KR | 10-1375018 B1 | | 3/2014 | |
| KR | 10-2018-0116779 A | | 10/2018 | |
| KR | 10-2021-0099876 A | | 8/2021 | |
| KR | 2021099876 A | * | 8/2021 | ............ G16H 20/60 |

* cited by examiner

FIG. 4

| Name | Recipe | | Basic provision weight(g) | Nutrient per 100g | | | | | |
|---|---|---|---|---|---|---|---|---|---|
| | Basic ingredient | weight(g) | | Energy | Water | Protein | Lipoid | Aan | Carbohydrate |
| Cheonggu kjang jjigae | Water | 150 | 300 | 0 | 0 | 0 | 0 | 0 | 0 |
| | Garlic | 2 | | 123 | 65.3 | 7.03 | 0.12 | 0.90 | 26.61 |
| | Green onion | 3 | | 23 | 92.8 | 1.78 | 0.15 | 0.47 | 4.80 |
| | Pepper | 3 | | 29 | 91.1 | 1.71 | 0.19 | 0.58 | 6.42 |
| | Cheonggukjang | 50 | | 136 | 64.0 | 10.93 | 5.88 | 8.77 | 10.42 |
| | Kelp | 1 | | 12 | 91.0 | 1.1 | 0.2 | 3.5 | 4.2 |
| | Anchovy | 1 | | 125 | 73.4 | 17.7 | 5.4 | 3.2 | 0.3 |
| Stir-fried fork | Pork | 60 | 200 | 221 | 62 | 17.21 | 16.36 | 0.90 | 0.00 |
| | Onion | 20 | | 27 | 92 | 0.95 | 0.04 | 0.33 | 6.68 |
| | Ginger | 1 | | 42 | 88.2 | 0.97 | 0.15 | 0.86 | 9.82 |
| | Garlic | 5 | | 1234 | 65.3 | 7.03 | 0.12 | 0.90 | 26.61 |
| | Starch syrup | 15 | | 321 | 16.9 | 0.02 | 0 | 0.05 | 83.03 |
| | Soybean oil | 3 | | 915 | 0 | 0 | 99.31 | 0.03 | 0.66 |
| | Pepper paste | 10 | | 205 | 35.7 | 3.66 | 1.38 | 7.50 | 51.76 |
| | Green onion | 5 | | 16 | 94.3 | 1.5 | 0.1 | 0.9 | 3.2 |
| | Black pepper | 0.1 | | 362 | 11.5 | 12.87 | 5.00 | 4.34 | 66.33 |

...

SYSTEM AND METHOD FOR MEASURING DISH SIZE AND PROVIDING NUTRITION INFORMATION USING IMAGE RECOGNITION AND AUGMENTED REALITY BASED ON ARTIFICIAL INTELLIGENCE

CROSS-REFERENCE TO RELATED APPLICATION

A claim for priority under 35 U.S.C. § 119 is made to Korean Patent Application No. 10-2022-0106815 filed on Aug. 25, 2022 in the Korean Intellectual Property Office, the entire contents of which are hereby incorporated by reference.

BACKGROUND

1. Technical Field

The present disclosure relates to a system and a method for providing nutritional information. More specifically, the present disclosure relates to a system and a method for measuring dish size and providing nutritional information using image recognition and augmented reality based on artificial intelligence.

2. Description of Related Art

Recently, with the development of culture and an increase of international exchanges, obesity, various adult diseases, and other chronic diseases are increasing continuously due to a sudden change in eating habits, irregular meals, and insufficient exercise. Moreover, improvements in the quality of life, interest in health care suitable for lifestyles or environment changes is growing.

Accordingly, many people want to maintain their health in daily life, rather than relying on health care in hospitals. Thus, people have significant interest in eating habits which are the closest to health care. However, technical developments for managing the eating habits of a person are insufficient, and it is cumbersome that a person must search and record various pieces of information about food that the person is eating in order to manage his or her own eating habits.

Therefore, there is a need to develop a technology for automatically recording and analyzing an image including meal information of a user and generating and providing nutritional information according to the analysis result obtained using artificial intelligence.

PATENT LITERATURE

Patent Documents

Patent Document 1: Korean Patent No. 10-1375018 (Granted on Mar. 10, 2014)

SUMMARY

The present disclosure has been made to solve the above-mentioned problems occurring in the prior art, and in an aspect of the present disclosure, an object of the present disclosure is to provide a system and a method for measuring dish size and providing nutritional information using image recognition and augmented reality based on artificial intelligence, which can automatically record and analyze an image including meal information of a user and generate and provide nutritional information according to the analysis result obtained using artificial intelligence, thereby allowing a user to conveniently monitor his or her eating habits in real time.

The aspects of the present disclosure are not limited to those mentioned above, and other aspects not mentioned herein will be clearly understood by those skilled in the art from the following description.

To accomplish the above-mentioned objects, according to an aspect of the present disclosure, there is provided a system for measuring dish size and providing nutritional information using image recognition and augmented reality based on artificial intelligence, the system including: at least one imaging device acquiring at least one image including at least one dish or at least one food contained in each dish; a service providing apparatus for detecting the at least one dish and the at least one food from the at least one image when the at least one image is received, confirming the name of each detected food on the basis of a learning model, predicting the size of each detected dish, predicting the volume of each detected food using the predicted size of the dish, and generating nutritional information using the predicted volume of each food and pre-stored food information; and a user terminal for visualizing and displaying the nutritional information when the nutritional information is received.

According to another aspect of the present disclosure, there is provided a method for measuring dish size and providing nutritional information using image recognition and augmented reality based on artificial intelligence, the method including the operations of: classifying and detecting at least one dish and at least one food contained in each dish from at least one image when the at least one image is received; predicting the size of each detected dish based on a learning model; predicting the volume of each detected food using the predicted size of the dish based on the learning model; and generating nutritional information using the predicted volume of each food and pre-stored food information.

Besides the above, a computer program stored in a computer readable recording medium for embodying the present disclosure may additionally be provided.

Besides the above, a computer readable recording medium to record computer programs for executing the method may additionally be provided.

BRIEF DESCRIPTION OF THE DRAWINGS

FIG. 4 is a view illustrating an example of pre-stored food information according to an embodiment of the present disclosure.

DETAILED DESCRIPTION

Figure 1:
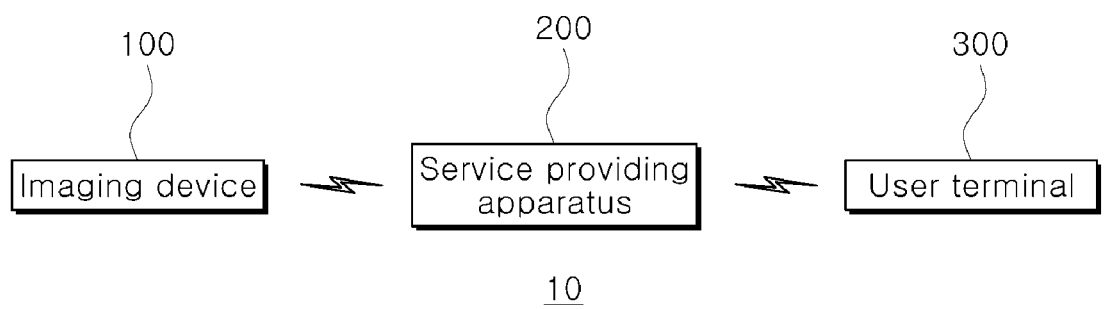
FIG. 1 is a view illustrating a network structure of a system for providing nutritional information based on image analysis using artificial intelligence according to an embodiment of the present disclosure.

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skill in the art can fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that the terms of 'include' or 'have' in the specification are used to mean that there is no intent to exclude existence or addition of other components besides components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

In the drawings, like reference numerals designate like components. This disclosure does not describe all components of embodiments, and general contents in the technical field to which the present disclosure belongs or repeated contents of the embodiments will be omitted. The terms, such as "unit, module, member, and block" may be embodied as hardware or software, and a plurality of "units, modules, members, and blocks" may be implemented as one component, or a unit, a module, a member, or a block may include a plurality of components.

Throughout this specification, when a part is referred to as being "connected" to another part, this includes "direct connection" and "indirect connection", and the indirect connection may include connection via a wireless communication network. Furthermore, when a certain part "includes" a certain component, other components are not excluded unless explicitly described otherwise, and other components may in fact be included.

Furthermore, when a certain part "includes" a certain component, other components are not excluded unless explicitly described otherwise, and other components may in fact be included.

In the entire specification of the present disclosure, when any member is located "on" another member, this includes a case in which still another member is present between both members as well as a case in which one member is in contact with another member.

The terms "first," "second," and the like are just to distinguish a component from any other component, and components are not limited by the terms.

The singular form of the components may be understood into the plural form unless otherwise specifically stated in the context.

Identification codes in each operation are used not for describing the order of the operations but for convenience of description, and the operations may be implemented differently from the order described unless there is a specific order explicitly described in the context.

Terms used in the following description will be defined as follows.

In description of the present disclosure, the present disclosure is limited to a service providing apparatus, but may further include a server, a computer and/or a portable terminal, or may be configured to have any form of the server, the computer and/or the portable terminal.

Here, the computer may include, for example, a notebook computer equipped with a web browser, a desktop, a laptop, a tablet PC, a slate PC, and the like.

The service providing apparatus is a server to process information by performing communication with an external device, and may include an application server, a computing server, a database server, a file server, a game server, a mail server, a proxy server, a web server, and the like.

The portable terminal is a wireless communication device providing portability and mobility, and includes all kinds of handheld-based wireless communication devices, such as a personal communications system (PCS), a global system for mobile communications (GSM) terminal, a personal digital cellular (PDC) terminal, a personal handphone system (PHS) terminal, a personal digital assistant (PDA), an international mobile telecommunications (IMT)-2000 terminal, a code division multiple access (CDMA)-2000 terminal, a W-code division multiple access (W-CDMA) terminal, wireless broadband internet (WiBro) terminal, a smartphone, and the like, and a wearable device, such as a watch, a ring, a bracelet, an ankle bracelet, a necklace, glasses, contact lenses, or a head-mounted device (HMD).

Hereinafter, operation principles and embodiments of the present disclosure will be described with reference to the accompanying drawings.

FIG. 1 is a view illustrating a network structure of a system for providing nutritional information based on image analysis (hereinafter, called 'image analysis-based nutritional information providing system') using artificial intelligence according to an embodiment of the present disclosure.

Referring to FIG. 1, an image analysis-based nutritional information providing system 10 using artificial intelligence according to an embodiment of the present disclosure may include an imaging device 100, a service providing apparatus 200, and a user terminal 300. However, for convenience of description, one imaging device 100 and one user terminal 300 are illustrated in the drawing, but a plurality of imaging devices 100 and a plurality of user terminals 300 may be provided, and types of terminals may also be the same or different. That is, types and the number of the imaging devices 100 and the user terminals 300 are not limited.

The imaging device 100 includes at least one camera, and obtains at least one image including at least one dish or at least one food contained in the at least one dish based on the at least one camera. In this instance, the imaging device 100 can be arranged and installed in a space where a user is eating. The imaging device 100 may be installed to be fixed or be movable, and is not limited in the shape thereof.

The imaging device 100 may perform imaging according to a request of a user, but may perform imaging by automatically sensing at least one among a user, a motion, and food to recognize a meal situation. In addition, after recognizing the meal situation, the imaging device 100 may be set to obtain an image including a dish or food before eating only once, or to periodically obtain images during a meal time. However, when obtaining images, not only one image but one or more images are obtained to enable more accurate recognition.

Meanwhile, the one or more images captured by the imaging device 100 may include at least one among a dish, food, and a user.

Specifically, the imaging device 100 includes at least one among a two-dimensional camera, a three-dimensional camera, a time-of-flight (ToF) camera, a light field camera, a stereo camera, an event camera, an infrared camera, a lidar sensor, and an array camera. In this instance, the imaging device 100 may include at least one camera (sensor), and the types of the cameras may be the same, but at least some of the various types of cameras described above may be combined.

In a case in which at least one image is received from the imaging device 100, the service providing apparatus 200 detects at least one food included in the at least one image, and confirms the name of each of the at least one detected food based on the learning model. Thereafter, the service providing apparatus 200 maps food information included in pre-stored food information on the basis of each confirmed name, and generates nutritional information obtained using the mapped food information.

Here, the pre-stored food information may include at least one among name information, recipe information, nutritional content information, and basic weight information on at least one food. The recipe information may include basic ingredient information including at least one ingredient necessary for cooking the relevant food, and weight information on each of the at least one ingredient. Meanwhile, the nutritional content information may include nutritional contents for each of the at least one ingredient and weight of each nutritional content.

Meanwhile, the service providing apparatus 200 may classify and manage meal information for each of at least one user. In a case in which at least one image for a specific user is received, the received at least one image may be cumulatively stored as meal information of the specific user. In this instance, the service providing apparatus 200 may generate and provide the meal information of the specific user in a preset periodic unit. Specifically, the meal information may be provided in periodic units of day, week, month, and the like. Even when the meal information is provided on a daily basis, the meal information may be divided and stored into breakfast, lunch, and dinner or may be divided and stored every point of time when the user has a meal. For example, the meal information may further include at least one among meal time information (eating date and time, a period of time required for the meal, etc.), meal pattern information, and preferred food information as well as image information, type information, intake information, nutrient information, and calorie information of the food that the user ate.

On the other hand, in a case in which a person is included in at least one image received from the imaging device 100, the service providing apparatus 200 identifies whether the person is a pre-stored user by recognizing biometric information (a face, an iris, etc.) of the person. Furthermore, in a case in which it is confirmed that the user is a pre-stored user, the service providing apparatus 200 stores at least one image and nutritional information, which is analyzed on the basis of the at least one image, into the pre-stored information (personal information, body information, disease information, allergy information, meal information, etc.) on the relevant user to update the information. Meanwhile, in a case in which it is confirmed that the user is not a pre-stored user, the service providing apparatus 200 registers the user as a new user on the basis of the information about the relevant user, and stores at least one image and nutritional information analyzed on the basis of the same. In this case, the service providing apparatus 200 may directly receive personal information, body information, disease information, and allergy information about the user from the user later, or may collect and store personal information, body information, disease information, and allergy information about the user from at least one institution or company.

In order to provide the aforementioned services, the service providing apparatus 200 can pre-learn a learning model on the basis of a sample image and a verification image, and then, can improve the performance of the learning model obtained using the at least one image received and stored from the imaging device 100.

The user terminal 300 is a user terminal for receiving services from the service providing apparatus 200, and the user is provided with a variety of information based on the meal information of the user through a specific webpage or application through the user terminal 300.

In a case in which the nutritional information is received from the service providing apparatus 200, the user terminal 300 visualizes the nutritional information and displays the same through a display unit provided in the user terminal 300 so that the user can easily confirm the nutritional information.

FIG. 1 illustrates that the imaging device 100 is disposed separately from the service providing apparatus 200 and the user terminal 300, but the imaging device 100 may be provided in at least one among a first form in which the imaging device 100 is disposed (connected) to the user terminal 300, a second form in which the imaging device 100 is disposed (connected) to the service providing apparatus 200, and a third form in which the imaging device 100 is arranged and installed in a specific space.

Figure 2:
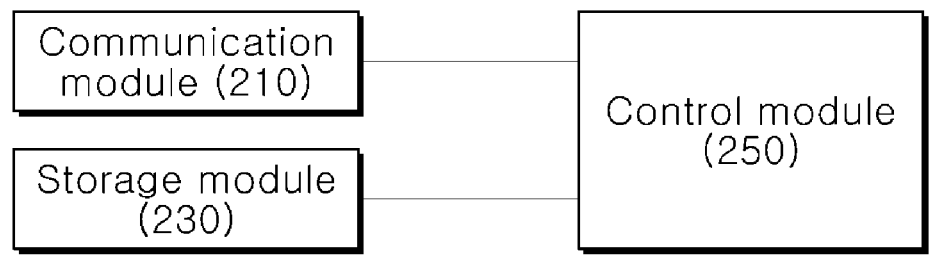
FIG. 2 is a view illustrating a configuration of a service providing apparatus for providing nutritional information based on image analysis using artificial intelligence according to an embodiment of the present disclosure.

FIG. 2 is a view illustrating a configuration of a service providing apparatus for providing nutritional information based on image analysis using artificial intelligence according to an embodiment of the present disclosure.

Referring to FIG. 2, the service providing apparatus for providing nutritional information based on image analysis using artificial intelligence (hereinafter, referred to as a "service providing apparatus") according to an embodiment of the present disclosure may include a communication module 210, a storage module 230, and a control module 250.

The communication module 210 may include one or more components enabling communication with an external device, and may include, for example, at least one among a wired communication module, a wireless communication module, and a short-range communication module, so as to transmit and receive a signal on the basis of the at least one communication module.

Here, the wired communication module may include not only various wired communication modules, such as a local area network (LAN) module, a wide area network (WAN) module, or a value added network (VAN) module, but also various cable communication modules, such as a universal serial bus (USB), a high definition multimedia interface (HDMI), a digital visual interface (DVI), a recommended standard 232 (RS-232), a power line communication, or a plain old telephone service (POTS).

The wireless communication module may support various wireless communication methods, such as global system for mobile communication (GSM), code division multiple access (CDMA), wideband code division multiple access (WCDMA), universal mobile telecommunications system (UMTS), time division multiple access (TDMA), long term evolution (LTE), and 4G, 5G, 6G and the like as well as a Wi-Fi module, a wireless broadband (Wibro) module.

The short-distance communication module may support short-distance communication using at least one among Bluetooth™, radio frequency identification (RFID), infrared data association (IrDA), ultra-wideband (UWB), ZigBee®, near field communication (NFC), wireless-fidelity (Wi-Fi), Wi-Fi Direct, and wireless universal serial bus (Wireless USB).

The storage module 230 may store data and/or various pieces of information supporting various functions of the service providing apparatus 200. The storage module 230 may store a plurality of application programs or applications running on the service providing apparatus 200, and data and instructions for operating the service providing apparatus 200. At least a portion of these applications may be downloaded from an external server via wireless communication. Meanwhile, application programs may be stored in at least one memory, and may be installed on the service providing apparatus 200 to perform operations or functions by at least one processor disposed in the control module 230.

Specifically, the at least one memory stores at least one machine learning model and at least one process to facilitate provision of nutritional information based on image analysis using artificial intelligence.

Meanwhile, the at least one memory may include a storage medium having at least one among a flash memory type memory, a hard disk type memory, a multimedia card micro type memory, a card type memory (e.g., an SD memory or an XD memory), a random access memory (RAM), static random access memory (SRAM), read-only memory (ROM), an electrically erasable programmable read-only memory (EEPROM), a programmable read-only memory (PROM), a magnetic memory, a magnetic disk, and an optical disk. Furthermore, the memory may store information temporarily, permanently, or semi-permanently, and may be disposed in an embedded type or a detachable type.

The control module 250 may include at least one processor, and may control all components in the service providing apparatus 200 to process input or output signals, data, information, and the like, execute instructions, algorithms, and application programs stored in the at least one memory to execute various processes, and provide or process appropriate information or functions for fault detection based on drop image analysis using artificial intelligence.

Specifically, in a case in which at least one image is received, the control module 250 detects at least one food included in the at least one image, and identifies the name of the detected at least one food on the basis of the learning model. In addition, the control module 250 maps food information included in the pre-stored food information based on the identified name, generates nutritional information obtained using the mapped food information, and transmits the nutritional information to the user terminal 300.

To generate nutritional information, the control module 250 generates recognized ingredient information by recognizing ingredients of the at least one food included in the at least one image, confirms basic ingredient information of each food from the mapped food information, and compares the basic ingredient information with the recognized ingredient information and performs collection of ingredients. Accordingly, the control module 250 can generate final ingredient information.

However, the control module 250 may not simply collect ingredients included in the recognition ingredient information and the basic ingredient information, but may perform an editing operation of removing the duplicated ingredients. That is, all of the ingredients included in the recognized ingredient information and the basic ingredient information are included, but the commonly included ingredients are included once.

In addition, in order to generate nutritional information, the control module 250 calculates the weight of each of the at least one ingredient included in the final ingredient information based on the at least one image and the pre-stored food information, generates nutrient information obtained using the calculated weight, and includes the nutrient information in the nutritional information. Specifically, the control module 250 detects the amount of food provided to the user obtained using the at least one image, and calculates the weight of the relevant food provided to the user obtained using the weight information of the relevant food included in the pre-stored food information.

Figure 3:
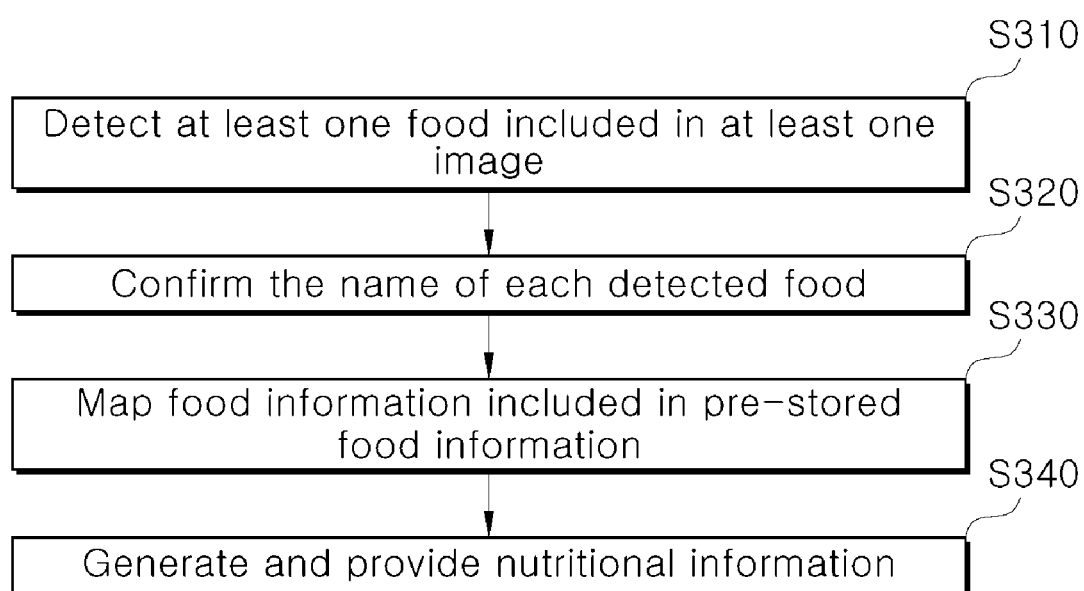
FIG. 3 is a view illustrating a method for providing nutritional information based on image analysis using artificial intelligence according to an embodiment of the present disclosure.

FIG. 3 is a view illustrating a method for providing nutritional information based on image analysis using artificial intelligence according to an embodiment of the present disclosure.

Referring to FIG. 3, in a case in which at least one image is received from the imaging device 100, the service providing apparatus 200 detects at least one food included in the at least one image (S310). In this instance, the service providing apparatus 200 confirms whether food exists in the at least one image, and uses only the image in which the food exists according to the confirmation result. In addition, the present disclosure may confirm the location of food as well as the existence of food.

Next, the service providing apparatus 200 confirms the name of the at least one food detected according to the operation S310 based on the learning model (S320), and performs mapping with the food information included in the pre-stored food information based on the confirmed name (S330). That is, the service providing apparatus 200 compares the name of the at least one food confirmed in operation S320 with pre-stored food information to detect relevant food information, and maps the pre-stored food information with the detected food information. As an example, the service providing apparatus 200 compares the name of the at least one food with the name included in the pre-stored food information to detect food information having a name which is equivalent or similar to the name of the pre-stored food information, and maps the detected food information with the relevant food.

As described above, the pre-stored food information includes name information, recipe information, nutritional content information, and basic weight information about the at least one food, and the nutritional information generated on the basis of the food information may include name information, final ingredient information, nutrient information, and weight information for the at least one food as well as the image information including the at least one food. In this instance, the weight information included in the nutritional information may include at least one among provision weight information, which is weight information of each food provided to the user, and intake weight information, which is weight information of each food that the user ate.

Next, the service providing apparatus 200 generates and stores nutritional information obtained using the food information mapped by the operation S330 (S340), and transmits the nutritional information to the user terminal 300.

As described above, the present disclosure confirms a variety of information based on the pre-stored food information. Hereinafter, confirmation of a variety of information will be described in detail with reference to FIG. 4, and the operation of generating nutritional information using the same will be described in detail.

FIG. 4 is a view illustrating an example of pre-stored food information according to an embodiment of the present disclosure.

Referring to FIG. 4, the pre-stored food information may include name information, recipe information, basic weight information, and nutritional content information as described above.

For instance, the food information for cheonggukjang jjigae (Rich soybean paste stew) is the recipe information, and may include information on basic ingredients and weight of each of the basic ingredients used for cooking the cheonggukjang jjigae, basic provision weight (g) basically provided when the cheonggukjang jjigae is provided, and various nutrients included per 100 g.

Meanwhile, not illustrated in FIG. 4, but the pre-stored food information may further include applied dish information which is information on a dish mainly applied for each food. In this instance, the dish applied has a size capable of containing food of the basic provision weight (g).

In order to generate and manage the pre-stored food information as database, the service providing apparatus 200 may learn a learning model on the basis of a preset dataset. Thereafter, the service providing apparatus 200 may repeatedly perform learning according to a preset period to improve the performance of the learning model using at least one image received from at least one user in order to generate nutritional information.

Figure 5:
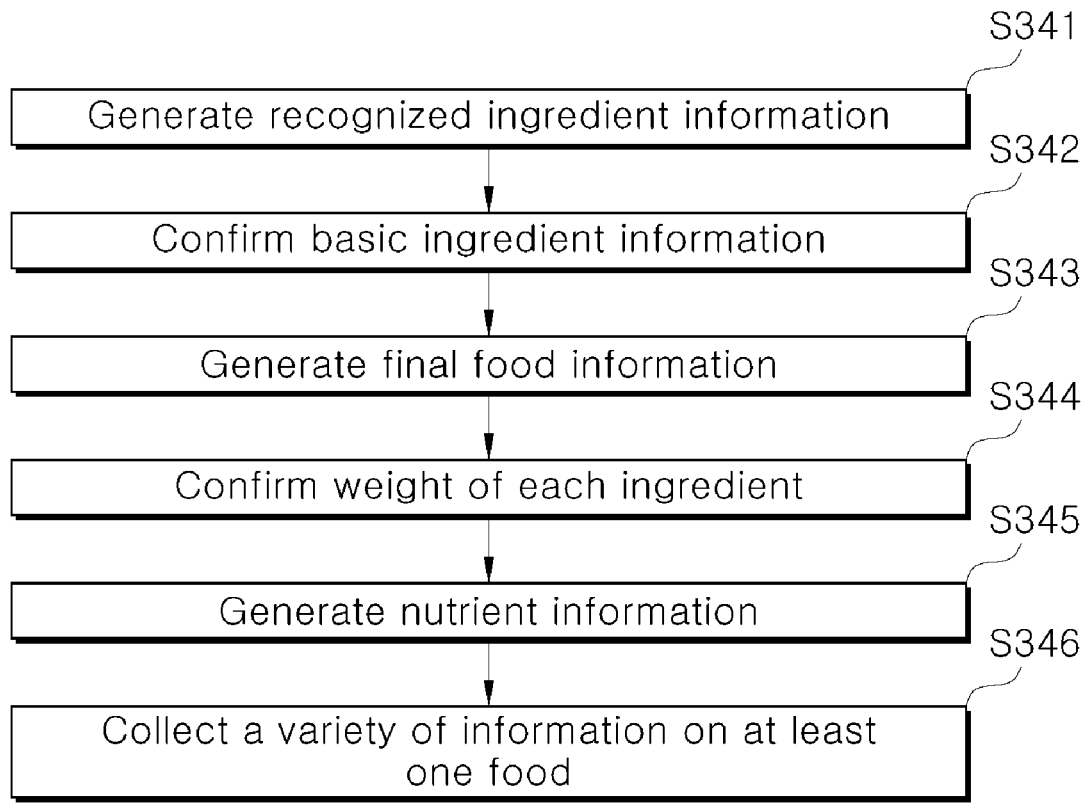
FIG. 5 is a view illustrating a specific operation of generating nutritional information according to an embodiment of the present disclosure.

FIG. 5 is a view illustrating a specific operation of generating nutritional information according to an embodiment of the present disclosure, and concretizes the operation S340 of FIG. 3.

Referring to FIG. 5, the service providing apparatus 200 generates recognized ingredient information by recognizing ingredients of at least one food detected on the basis of at least one image received by the operation S310 (S341). In this instance, weight of each ingredient may be also recognized. In this instance, the recognized ingredient information may include ingredients for each detected food and weight corresponding to each ingredient.

Next, the service providing apparatus 200 confirms the basic ingredient information of each detected food from the pre-stored food information (S342). Specifically, the service providing apparatus 200 may confirm the recipe information of the relevant food on the basis of the food information mapped by the operation S330, and directly calculate the basic provision weight on the basis of the basic ingredient information of the relevant food and the weight information of each basic ingredient based on the recipe information, or may confirm the basic provision weight included in the food information.

Next, the service providing apparatus 200 generates final ingredient information using the recognized ingredient information generated in operation S341 and the basic ingredient information confirmed in operation S342 (S343). Specifically, the service providing apparatus 200 collects ingredients included in the recognized ingredient information and the basic ingredient information in such a way that commonly included ingredients are included once, and generates final ingredient information so that the ingredients do not overlap.

For example, in a case in which cheonggukjang jjigae included in an image was detected and the service providing apparatus 200 recognized ingredients from a cheonggukjang jjigae-related image cropped from the image to generate final ingredient information, if tofu, autumn squash, and green onion are further included in the recognized ingredients, although the basic ingredients of the cheonggukjang jjigae in the pre-stored food information of FIG. 4 do not include the recognized ingredients, the service providing apparatus 200 may generate final ingredient information by adding the recognized ingredients.

Accordingly, even though the recognized ingredients are not included in the basic ingredient information, a user may recognize and further use the added ingredients when cooking the relevant food, and may use ingredients, which are not recognized by the image, for instance, liquid type or powder type seasoning, on the basis of the basic ingredient information. Therefore, the service providing apparatus 200 may generate nutritional information approaching the food which the user ate actually.

Next, the service providing apparatus 200 confirms weight of each ingredient included in the final ingredient information generated by the operation S343 on the basis of the at least one image and the pre-stored food information (S344), and generates nutrient information of the relevant food using nutritional contents of each of the confirmed ingredients and weight of each nutritional content (S345). Here, ingredients included in the final ingredient information may not be included in the basic ingredient information, but may be included in ingredients recognized through the relevant image. In this case, since weight of the recognized ingredient cannot be confirmed through the food information of the relevant food, weight of the recognized ingredient recognized through the relevant image may be used. In this instance, the ingredient recognized through the relevant image is recognized when the recognized ingredient information is generated, and the nutrient information may be calculated and generated with respect to weight of each of the basic ingredients included in the final ingredient information based on nutritional contents, which are included in the pre-stored food information, and weight of each of the nutritional contents, and weight of each of the recognized ingredients.

The operations from S341 to S345 are performed with respect to each of the at least one food detected in operation S310. After the operation S345, the service providing apparatus 200 generates nutritional information by collecting a variety of information on each food (S346). Specifically, the operation S346 may be performed additionally in a case in which there are a number of detected foods. In a case in which there is one detected food, there is no need to collect a variety of information on each food, so it is possible to omit the operation S346.

Meanwhile, when collecting a variety of information on each food in the operation S346, the service providing apparatus 200 may generate nutritional information by establishing a variety of information on at least one food detected by the operation S310 on the basis of a preset format, but may generate integrated information in which a variety of information on at least one food is integrated and add the integrated information to the nutritional information.

Therefore, the nutritional information may include at least one among name information, basic ingredient information, recognized ingredient information, final ingredient information, weight information, and nutrient information for each food which the user ate, and further include integrated information generated by integrating (summing) the pieces of information.

Meanwhile, the service providing apparatus 200 may calculate weight of the relevant food on the basis of the basic provision weight and perform correction thereof when generating the nutrient information in operation S345. Now, referring to FIG. 6, concrete operations will be described.

Figure 6:
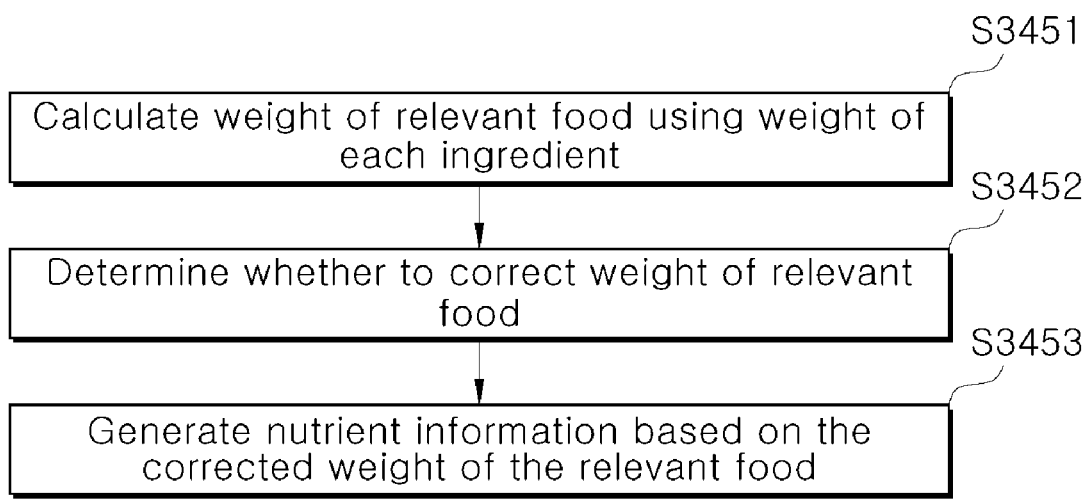
FIG. 6 is a view illustrating a specific operation of generating nutrient information according to another embodiment of the present disclosure.

FIG. 6 is a view illustrating a specific operation of generating nutrient information according to another embodiment of the present disclosure, and concretizes the operation S345 of FIG. 5.

The service providing apparatus 200 calculates the weight of the relevant food obtained using the weight of each ingredient confirmed by the operation S344 (S3451), and determines whether to correct the weight of the relevant food based on the pre-stored food information (S3452).

Specifically, the weight of the relevant food is determined by comparing the weight of the relevant food with the basic provision weight corresponding to the food. As a result of the comparison, it is determined to perform correction in a case in which the weight of the relevant food deviates from the basic provision weight. Moreover, as a result of the comparison, it is determined that the correction is not performed in a case in which the weight of the relevant food does not deviate from the basic provision weight.

Here, the basic provision weight may be set using at least one of the minimum provision weight and the maximum provision weight, or may be provided in a provision weight range on the basis of the minimum provision weight and the maximum provision weight. Meanwhile, the basis provision weight may be set using at least one of the minimum allowable weight and the maximum allowable weight of food which is containable in a relevant dish, or may be provided in an allowable weight range set on the basis of the minimum allowable weight and the maximum allowable weight. That is, the basic provision weight is set in consideration of dishes provided according to characteristics of each food. In this case, the basis provision weight may be pre-defined in the pre-stored food information, may be calculated on the basis of the applied dish information included in the pre-stored food information, or may be calculated by detecting dish information on at least one dish included in the at least one image when detecting the at least one food included in the at least one image in operation S310.

In this instance, in a case in which it is determined to correct the weight of the relevant food by the operation of S3452, the service providing apparatus 200 may correct weight of all or a portion of ingredients included in the final ingredient information of the relevant food. For instance, the service providing apparatus 200 may correct the weight of the relevant food obtained using at least one among a first correction method of correcting weight of all ingredients except water out of various ingredients included the final ingredient information, a second correction method of correcting only the weight of the recognized ingredients except water and the basic ingredients, and a third correction method of correcting weight of all ingredients in proportion. Meanwhile, the service providing apparatus 200 may correct weight of the relevant food except weight of ingredients, such as garnish, in the final ingredient information. So, the preset food information may further include classification information of each ingredient included in each food.

Next, the service providing apparatus 200 generates nutrient information based on the weight of the relevant food which was corrected or was not corrected according to the determination of the operation S3452 (S3453). In this instance, the nutrient information may be generated obtained using the nutritional content information included in the preset food information.

Meanwhile, according to another embodiment of the present disclosure, as illustrated in FIG. 6, the service providing apparatus may first generate nutritional information by correcting the weight of the relevant food, and second generate nutritional information in consideration of the volume of food predicted on the basis of the dish information of the relevant dish as necessary. That is, in a case in which a difference value between the weight of the corrected food and the weight according to the volume of the predicted food does not deviate from a preset threshold range, it is not necessary to secondarily generate nutritional information, and the first generated nutritional information may be provided to the user terminal 300 as the final nutritional information. Meanwhile, in another embodiment, since the dish information should be used, at least one dish may be detected when at least one food included in at least one image is detected. A specific operation thereof will be described below with reference to FIGS. 7 to 13.

Hereinafter, a method for providing nutritional information based on image analysis using artificial intelligence according to another embodiment will be described in detail with reference to FIG. 7.

Figure 7:
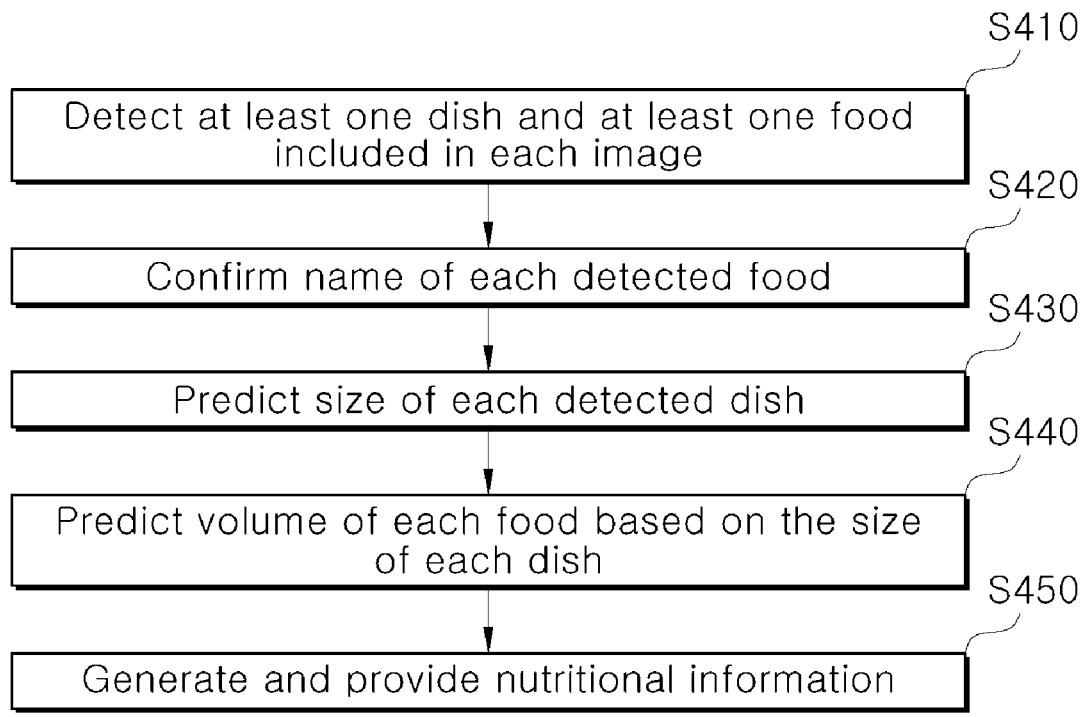
FIG. 7 is a view illustrating a method for providing nutritional information based on image analysis using artificial intelligence according to another embodiment of the present disclosure.

FIG. 7 is a view illustrating a method for providing nutritional information based on image analysis using artificial intelligence according to another embodiment of the present disclosure.

Referring to FIG. 7, in a case in which at least one image is received from the imaging device 100, the service providing apparatus 200 separately detects at least one dish and at least one food included in the at least one image (S410).

Next, the service providing apparatus 200 confirms the name of the at least one food detected by the operation S410 based on the learning model (S420), and predicts the size of the at least one dish detected by the operation S410 obtained using the pre-stored dish information (S430). In this case, FIG. 7 illustrates the operation S420 before the operation S430, but the operation S420 may be performed at the same time with the operation S430 or the operation S430 may be performed before the operation S420. That is, it doesn't matter in the order of performing the operations.

Next, the service providing apparatus 200 predicts the volume of each food detected in the operation S410 using the size of each dish predicted by the operation S430, and generates nutritional information using the volume of the food contained in each dish and the pre-stored food information (S450).

Specifically, when performing the operation S450, the operations of FIGS. 5 and 6 are firstly performed to primarily generate nutritional information for the relevant food, and then, nutritional information on the relevant food is secondarily generated using the volume of each food predicted by the operation S440. In this instance, the nutritional information secondarily generated may be generated by correcting the weight of the relevant food corrected by the operation S3452 in consideration of the volume of the relevant food predicted by the operation S440.

That is, as in the operation S330, the service providing apparatus 200 performs mapping with food information included in pre-stored food information through the name of each food confirmed in the operation S420 to calculate weight by confirming a variety of information on each food. In this instance, the service providing apparatus generates the final nutritional information by correcting the calculated weight in consideration of the actual volume of the relevant food contained in each dish.

Meanwhile, the present disclosure may use various methods to predict the size of each dish. Hereinafter, referring to FIGS. 8 to 13, the operation of predicting the size of a dish using a first method or a second method and the operation of measuring the volume of each food using the predicted size of the dish will be described in detail.

Figure 8:
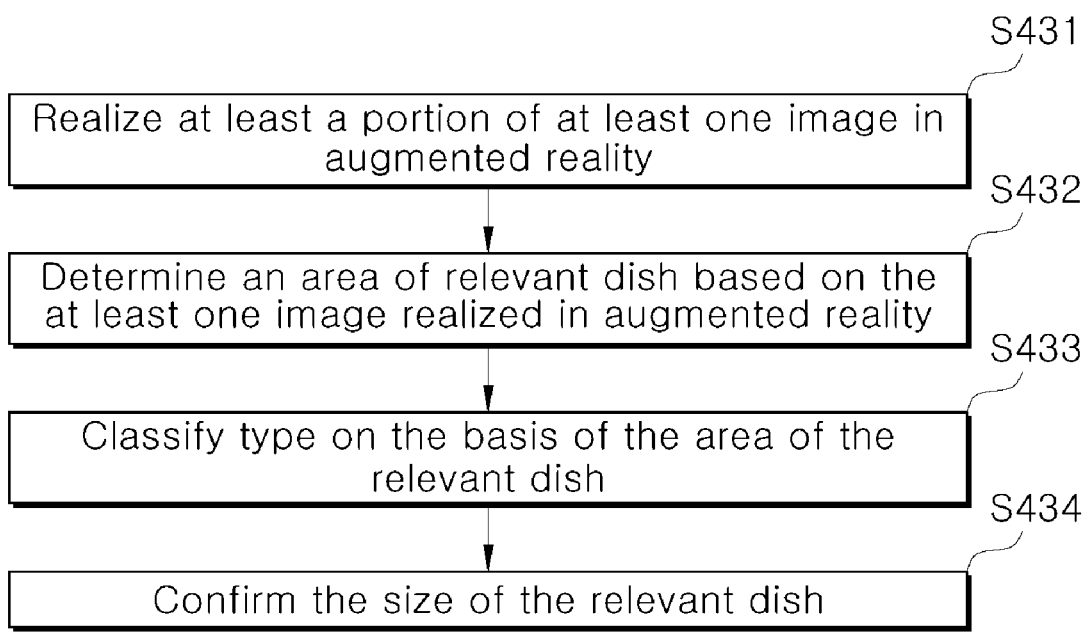
FIG. 8 is a view illustrating a specific operation of predicting the size of each dish according to a first method in the method for providing nutritional information based on image analysis using artificial intelligence according to another embodiment of the present disclosure.
Figure 9:
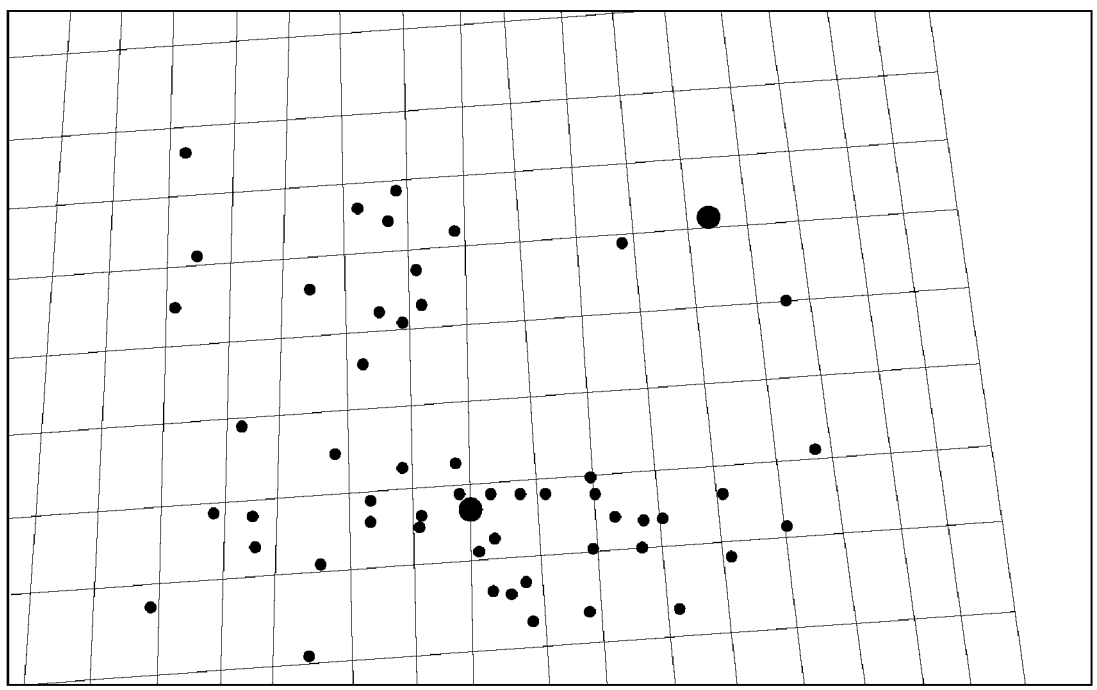
FIG. 9 is a diagram illustrating an example of an image realized on the basis of augmented reality to predict the size of each dish according to the first method in the method for providing nutritional information based on image analysis using artificial intelligence according to another embodiment of the present disclosure.

FIG. 8 is a view illustrating a specific operation of predicting the size of each dish according to a first method in the method for providing nutritional information based on image analysis using artificial intelligence according to another embodiment of the present disclosure, and concretizes the operation S430 of FIG. 7. Here, the first method is a method of using an image realized on the basis of augmented reality. Meanwhile, FIG. 9 is a diagram illustrating an example of an image realized on the basis of augmented reality to predict the size of each dish according to the first method in the method for providing nutritional information based on image analysis using artificial intelligence according to another embodiment of the present disclosure.

Referring to FIG. 8, the service providing apparatus 200 realizes at least a portion of at least one image including a relevant dish based on augmented reality (S431), and determines an area of the relevant dish based on the at least one image realized in the augmented reality (S432). Specifically, in a case in which an image is realized in augmented reality, a grid may be displayed on the relevant image as illustrated in FIG. 9, and an area of each dish included in the relevant image may be determined based on the size of the grid. In this instance, in connection with the grid in which there is a severe deviation in width and height, the service providing apparatus 200 may automatically perform correction.

Next, the service providing apparatus 200 classifies the type of the relevant dish based on the determined area (S433), and confirms the size of the relevant dish through the pre-stored dish information based on the type of the relevant dish (S434). That is, the size of the relevant dish can be confirmed on the basis of the dish information corresponding to the type of the relevant dish in the pre-stored dish information.

However, this is just an embodiment, and not only the area of the relevant dish but also the height of the relevant dish can be confirmed on the basis of the image realized in augmented reality. In this case, since the type of the relevant dish is classified using all of the area and the height, it can improve accuracy. That is, in order to classify the type of the relevant dish, at least one of the area and the height of the relevant dish determined through the image realized in augmented reality can be used, and the present disclosure is not limited thereto.

Figure 10:
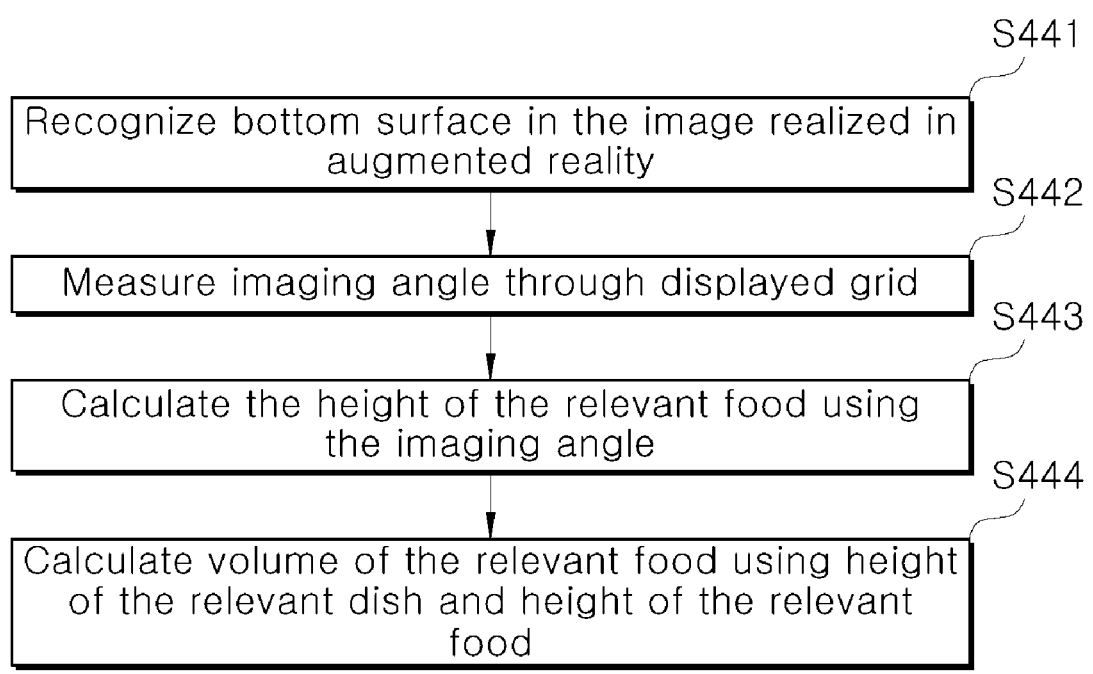
FIG. 10 is a view illustrating a specific operation of predicting the volume of the relevant food on the basis of the size of each dish predicted according to the first method in the method for providing nutritional information based on image analysis using artificial intelligence according to another embodiment of the present disclosure.

FIG. 10 is a view illustrating a specific operation of predicting the volume of the relevant food on the basis of the size of each dish predicted according to the first method in the method for providing nutritional information based on image analysis using artificial intelligence according to another embodiment of the present disclosure, and concretizes operation S440 of FIG. 7.

Referring to FIG. 10, the service providing apparatus 200 recognizes a bottom surface (or a table surface) from the image realized in augmented reality by operation S431 (S441), and measures an imaging angle thereof (S442). In this instance, a virtual surface for recognizing the floor surface may be displayed on the image.

Next, the service providing apparatus 200 calculates the height of the relevant food contained in the relevant dish obtained using the imaging angle measured by operation S442 (S443), and calculates the volume of the relevant food using the calculated height and the size of the relevant dish confirmed by operation S434 of FIG. 8 (S444).

Figure 11:
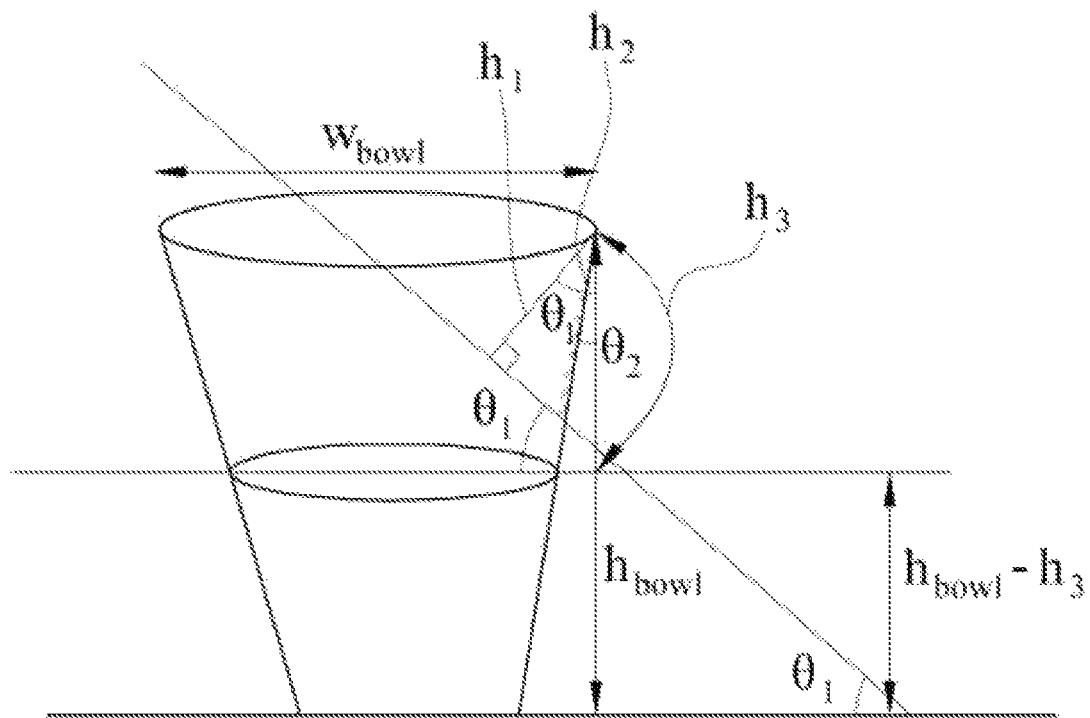
FIG. 11 is a diagram illustrating an example for calculating the volume of the relevant food contained in a relevant dish based on an imaging angle according to another embodiment of the present disclosure.

FIG. 11 is a diagram illustrating an example for calculating the volume of the relevant food contained in a relevant dish based on an imaging angle according to another embodiment of the present disclosure, and corresponds to an example of operation S443 of FIG. 10.

Referring to FIG. 11, the service providing apparatus 200 recognizes the bottom surface (or the table surface) from the image realized in augmented reality, and measures an imaging angle ($\theta_1$) of the imaging device 100.

Furthermore, the service providing apparatus 200 determines an area based on a width ($W_{bowl}$) of the relevant dish on the basis of the image realized in augmented reality, classifies the type of the relevant dish using the pre-stored dish information on the basis of the width ($W_{bowl}$), and confirms the size of the relevant dish to confirm the wall slope ($\theta_2$), the height ($h_{bowl}$), and the like of the relevant dish.

On the other hand, a height (h2) and a height (h3) are calculated using the following <Equation 1> based on the confirmed size of the relevant dish. Here, $H_2$ and $H_3$ mean a difference value between the maximum height of the relevant dish and the height of the relevant food, wherein $h_2$ is a value in which the wall slope of the relevant dish is considered, and $h_3$ is a value obtained without considering the wall slope.

$$h_2 = \frac{h_1}{\cos(\theta_1 - \theta_2)} \quad \text{[Equation 1]}$$

$$h_3 = h_2 \times \cos\theta_2 = h_1 \times \frac{\cos\theta_2}{\cos(\theta_1 - \theta_2)}$$

Thereafter, the height ($h_{food}$) of the relevant food may be calculated using the height ($h_{bowl}$) and the height ($h_3$) of the relevant dish, and may be indicated by the following <Equation 2>.

$$h_{food} = h_{bowl} - h_3 = h_{bowl} - h_1 \times \frac{\cos\theta_2}{\cos(\theta_1 - \theta_2)} \quad \text{[Equation 2]}$$

Therefore, the volume of the actual food contained in the relevant dish is determined as the volume of the final food.

Figure 12:
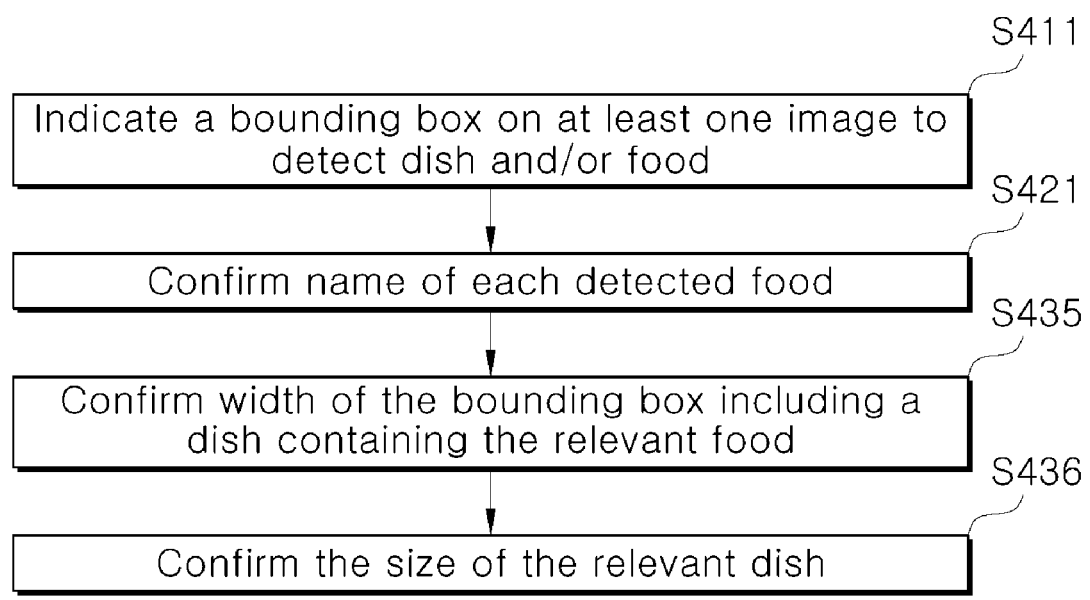
FIG. 12 is a view illustrating a specific operation of predicting the size of each dish according to a second method in the method for providing nutritional information based on image analysis using artificial intelligence according to another embodiment of the present disclosure.

FIG. 12 is a view illustrating a specific operation of predicting the size of each dish according to a second method in the method for providing nutritional information based on image analysis using artificial intelligence according to another embodiment of the present disclosure, and concretizes operations S410 to S430 of FIG. 7. Here, the second method is a method of displaying a bounding box on the image.

Referring to FIG. 12, the service providing apparatus 200 displays a bounding box for each object included in each image in operation S410, and performs labeling by detecting a dish and/or food among objects in the bounding box (S411).

Next, the service providing apparatus 200 confirms the name of each food detected by operation S411 (S421).

Next, the service providing apparatus 200 confirms the width of the bounding box including the dish in which the relevant food is contained in operation S430 (S435), and confirms the size of the relevant food by classifying the type of the relevant dish based on the confirmed width and characteristics of the food (S436). That is, the service providing apparatus 200 confirms the size of the relevant dish by confirming dish information corresponding to the type of the relevant dish on the basis of the pre-stored dish information. In this instance, in order to confirm an area of the bounding box, a grid which is any one among a transparent type, a translucent type, and an opaque type may be further displayed on the relevant image. In this instance, the grid may divide the screen at equal intervals.

However, this is just an embodiment, and when classifying the type of the relevant dish, at least one of the width and the shape may be considered, and the characteristics of the food may not be considered.

Figure 13A:
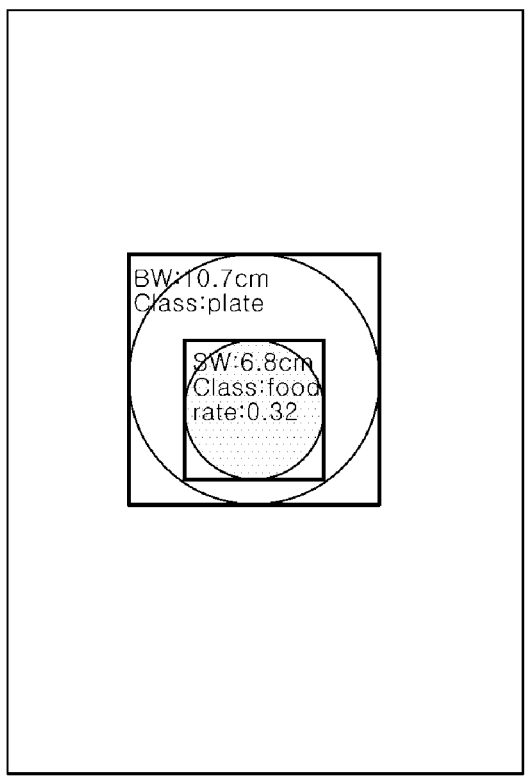
FIGS. 13A and 13B are diagrams illustrating an example of an image displaying a bounding box to predict the size of each dish according to the second method in the method for providing nutritional information based on image analysis using artificial intelligence according to another embodiment of the present disclosure.
Figure 13B:
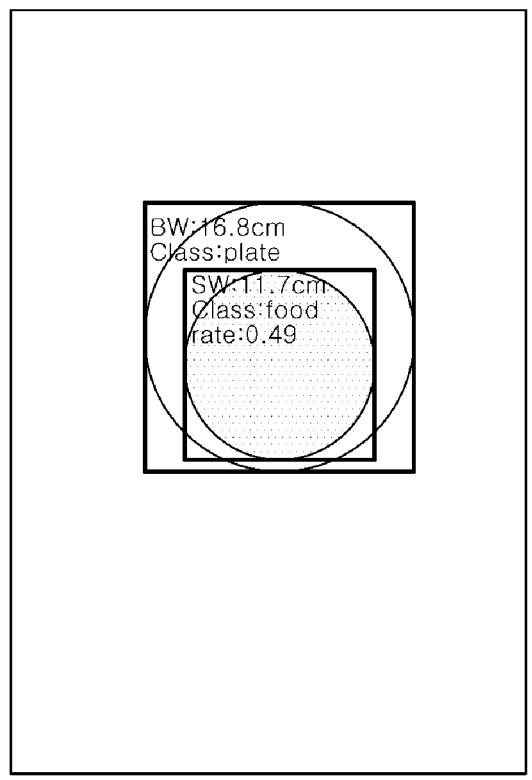

FIGS. 13A and 13B are diagrams illustrating an example of an image displaying a bounding box to predict the size of each dish according to the second method in the method for providing nutritional information based on image analysis using artificial intelligence according to another embodiment of the present disclosure.

As illustrated in FIGS. 13A and 13B, in a case in which an image is acquired by capturing an image of a dish containing liquid food from the top, a dish and food are detected from each image, and are indicated with bounding boxes. Thereafter, the width of each bounding box and the type of the relevant dish are labelled. Furthermore, an overlapping rate (IOU) between the bounding box of the relevant dish and the bounding box of the food contained in the dish may be labelled.

In this case, in order to predict the volume of the actual food contained in the relevant dish, the volume (capacity) of the relevant dish is calculated. In this instance, the volume of the relevant dish can be calculated by the following <Equation 3>.

$$V_{plate} = \begin{cases} I_O U * V_{full} & \text{if } I_O U \leq T_{max} \\ T_{max} * V_{full} & \text{if } T_{max} \leq I_O U \end{cases} \quad \text{[Equation 3]}$$

Here, IOU is an overlapping rate between the bounding box of the relevant dish and the bounding box of the food contained in the dish, $T_{max}$ is a maximum value of the IOU for the relevant dish and the relevant food, and $V_{full}$ represents the maximum capacity (ml) of the relevant dish.

In this instance, $V_{full}$ can be defined differently according to the type of the relevant dish.

For example, in a case in which the relevant dish is a bowl, $V_{full}$ may be expressed by the following <Equation 4>.

$$V_{full} = \frac{h_{predict}}{6}\left(3\left(\frac{d}{2}\right)^2 + h_{predict}^2\right)\pi \quad \text{[Equation 4]}$$

In a case in which the relevant dish is a plate, $V_{full}$ can be expressed by the following <Equation 5>.

$$V_{full} = \left(\frac{d}{2}\right)^2 h_{predict} \pi \quad \text{[Equation 5]}$$

In the Equation 4 and Equation 5, d represents the diameter of the relevant dish, $h_{predict}$ indicates the height of the relevant dish. In this instance, as the height of the relevant dish is pre-defined as the pre-stored dish information, the height of the relevant dish can be confirmed through the pre-stored dish information.

That is, the service providing apparatus 200 extracts area information obtained using the width of each bounding box including food or a dish containing the relevant food so as to calculate the volume of the food contained in the relevant dish.

Meanwhile, when weight of the relevant food is corrected on the basis of the dish information of the relevant dish, the correction may be performed based on the following <Equation 6> and <Equation 7>.

First, the weight of the relevant food corrected in consideration of the allowable volume of the relevant dish can be expressed by the following <Equation 6>.

$$W_{unit} = \frac{W_{food}}{V_{unitplate}}$$ [Equation 6]

Here, the $W_{food}$ is a reference weight (g) of the relevant food calculated on the basis of the pre-stored food information, and $V_{unitplate}$ is an allowable volume (ml) of the relevant dish which can be confirmed on the basis of the pre-stored dish information.

Meanwhile, the weight of the relevant food calculated in consideration of the volume of the actual food contained in the relevant dish with respect to the corrected weight of the food may be indicated by the following <Equation 7>.

$$W = V_{plate} \times W_{unit}$$ [Equation 7]

Here, W is the weight of the actual food contained in the relevant dish, and the $V_{plate}$ is the volume of the actual food contained in the relevant dish.

As described above, in order to perform each operation of FIGS. 7 to 13, the service providing apparatus 200 needs the pre-stored dish information. In this instance, the pre-stored dish information may include at least one among classification information, type information, size information (width, height, etc.), rate information (information about a food rate of each dish), weight information, allowable weight information, allowable volume information, minimum area information, and maximum area information with respect to at least one dish. However, sorts of information are not limited, and may be changed and set by a manager or a user. The following <Table 1> shows an example of the pre-stored dish information.

TABLE 1

| Category | Type | Allowable weight/ Allowable volume | Rate | Minimum Area | Maximum Area |
|---|---|---|---|---|---|
| Bowl | Small Bowl | 150 g | 0.71 | — | 80 |
| | Medium Bowl | 210 g | 1.00 | 81 | 120 |
| | Big Bowl | 250 g | 1.19 | 121 | 168 |
| | Soup Bowl | 250~400 ml | 1.55 | 169 | 224 |
| | Wide Bowl | 400~600 ml | 2.38 | 224 | 255 |
| | Noodle Bowl | ~800 ml | 3.81 | 256 | — |
| | Earthen Pot | 600~700 ml | 3.10 | 169 | 224 |
| Cup | Cup | 200 ml | 0.8 | — | — |
| | Mug | 355 ml | 1.42 | — | — |
| | Beer Glass | 500 ml | 2 | — | — |
| Food tray | Small tray | — | 3.6 | 0 | 35 |
| | Big tray | — | 5.2 | 35 | 9999 |
| Plate | Mini Plate | ~50 g | 0.6 | — | 63 |
| | Small Plate | 50~100 g | 0.9 | 64 | 168 |

TABLE 1-continued

| Category | Type | Allowable weight/ Allowable volume | Rate | Minimum Area | Maximum Area |
|---|---|---|---|---|---|
| | Medium Plate | 100~150 g | 1.47 | 169 | 288 |
| | Big Plate | 150 g~300 g | 1.8 | 289 | 440 |
| | Buffet Plate | 300 g~ | 2.25 | 441 | — |

Figure 14:
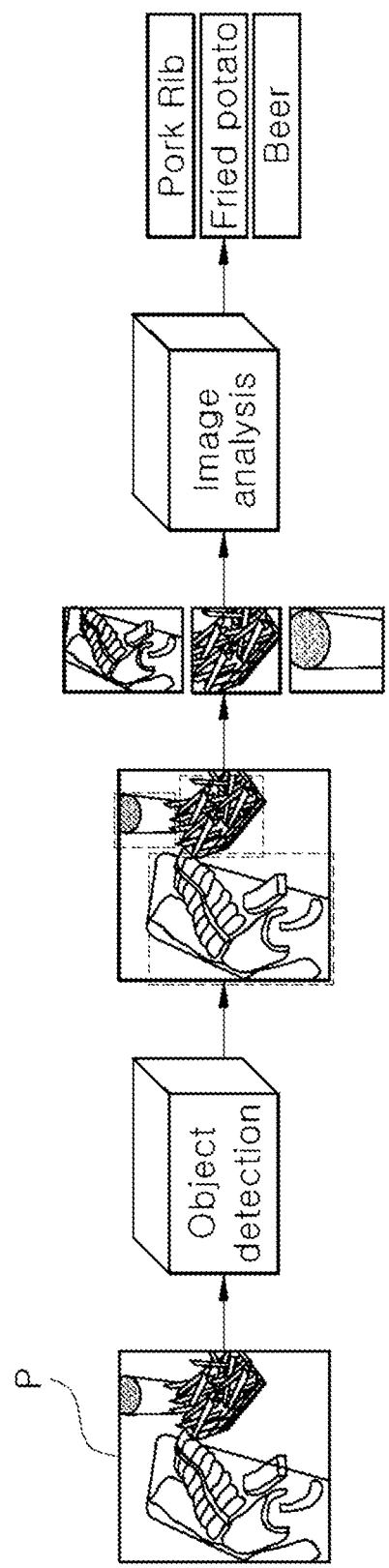
FIG. 14 is a view illustrating a series of operations of identifying names of foods based on an image received from an imaging device according to an embodiment of the present disclosure.

FIG. 14 is a view illustrating a series of operations of identifying names of foods based on an image received from an imaging device according to an embodiment of the present disclosure.

Referring to FIG. 14, in a case in which an image (P) is received from the imaging device 100, the service providing apparatus 200 detects at least one object included in the image (P). The detected object may be at least one among dishes and food.

Meanwhile, the image may be cropped and provided for each detected object, and each of the cropped images is analyzed to confirm food information of each object on the basis of the pre-stored food information. Accordingly, at least one among the name, recipe, nutrients, and weight of the food can be confirmed.

FIG. 14 illustrates only one of the images (P) received from the imaging device 100, but it is just for convenience in description, and at least one image (P) including the same dish and/or food may be received, thereby enabling more accurate analysis.

FIGS. 15A to 15D are views illustrating an example of detecting at least one dish and/or at least one food from the image received from the imaging device according to an embodiment of the present disclosure.

Figure 15A:
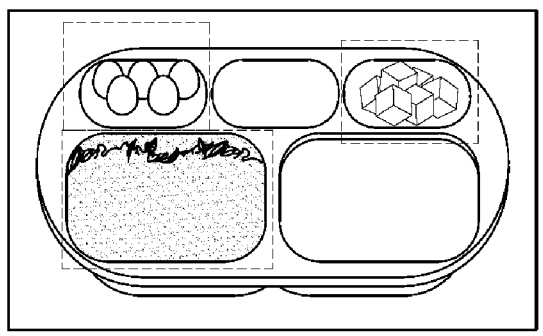
FIGS. 15A to 15D are views illustrating an example of detecting at least one dish and/or at least one food from the image received from the imaging device according to an embodiment of the present disclosure.
Figure 15B:
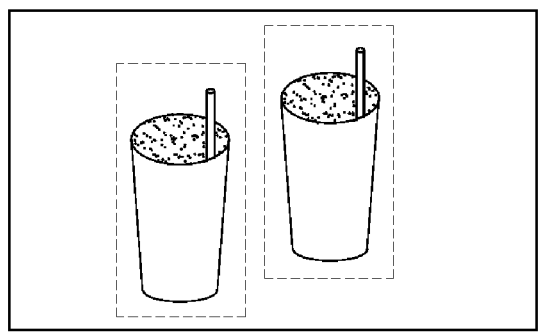
Figure 15C:
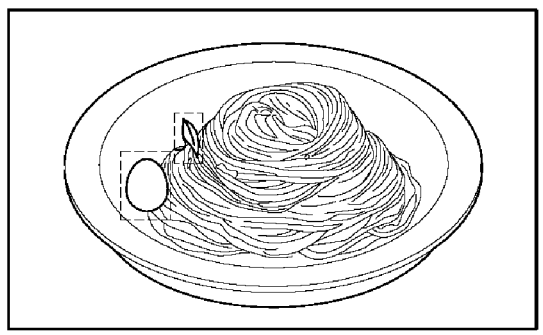

As illustrated in FIGS. 15A to 15D, the service providing apparatus 200 may receive various types of images from the imaging device 100. An image including a plurality of food items contained in one dish may be provided as illustrated in FIG. 15A, or an image including one food contained in one dish may be provided as illustrated in FIG. 15C. Moreover, the image of FIG. 15C includes additional ingredients, and the additional ingredients may be detected as recognized ingredients when the final ingredient information is generated.

Figure 15D:
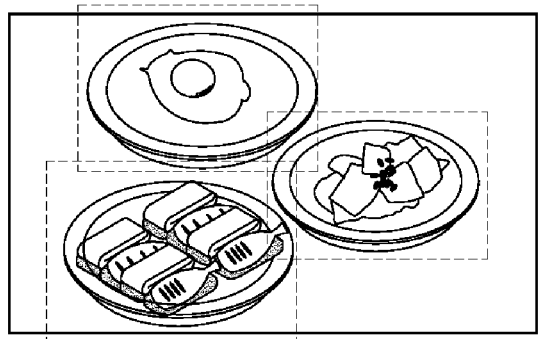

In addition, an image including a plurality of liquid food items contained in one dish may be provided as illustrated in FIG. 15B, or an image including a plurality of dishes and foods respectively contained in the plurality of dishes may be provided as illustrated in FIG. 15D.

The service providing apparatus 200 classifies and detects dishes and/or foods from such images. As illustrated in FIGS. 15A to 15D, the service providing apparatus 200 may classify and detect at least one dish (a dotted line box) included in each image and/or at least one food (solid line box) contained in each dish.

Figure 16:
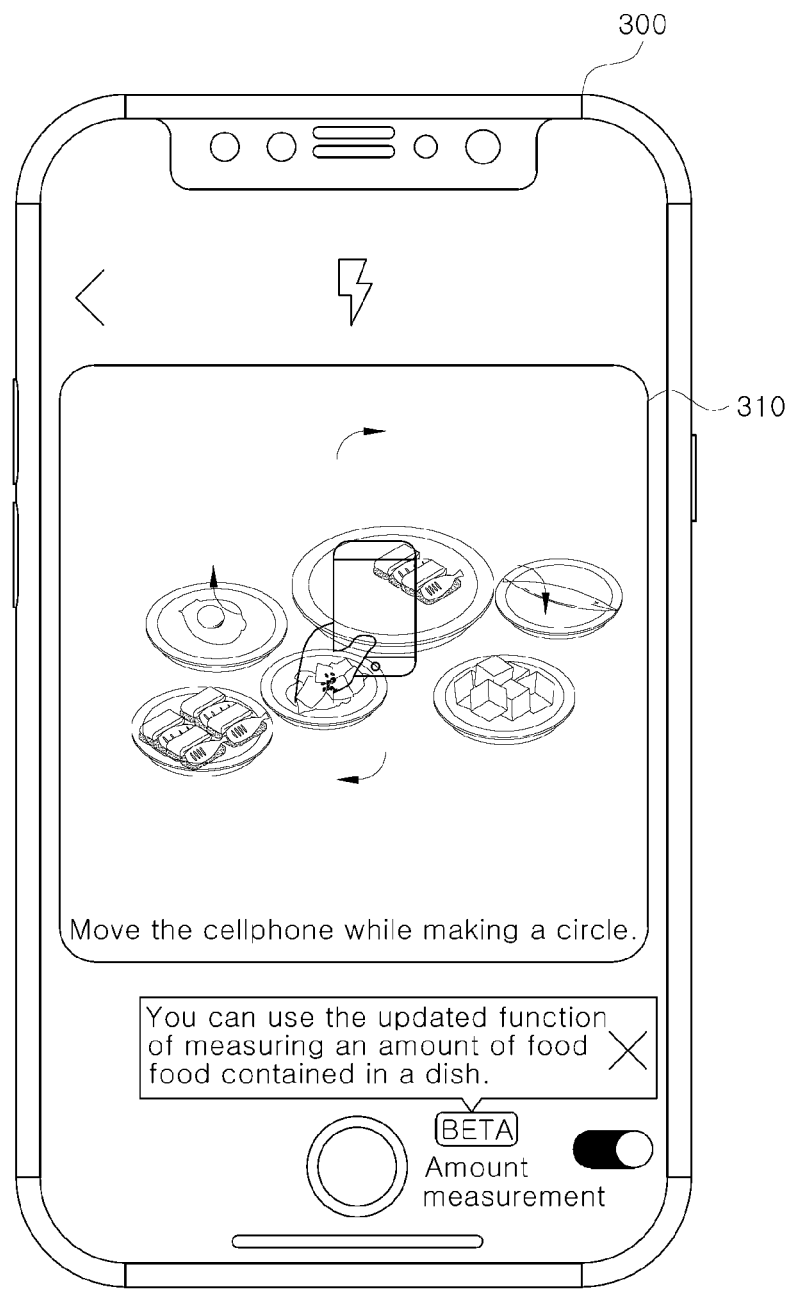
FIG. 16 is a view illustrating an example of a screen displayed on a display unit when capturing an image including a dish and/or food through the imaging device according to an embodiment of the present disclosure.

FIG. 16 is a view illustrating an example of a screen displayed on a display unit when capturing an image including a dish and/or food through the imaging device according to an embodiment of the present disclosure, which relates to the first form described above. In the first form, the imaging device 100 is disposed on the user terminal 300.

In this instance, an image to be captured, and a phrase or an image for guiding image-capturing may be displayed on the display unit 310 of the user terminal 300, and a button allowing the user to set imaging conditions may be displayed.

In this instance, the user terminal 300 may perform imaging through an application for a service provided from the service providing apparatus 200, or may perform imaging through a camera application disposed in the user terminal 300.

Figure 17:
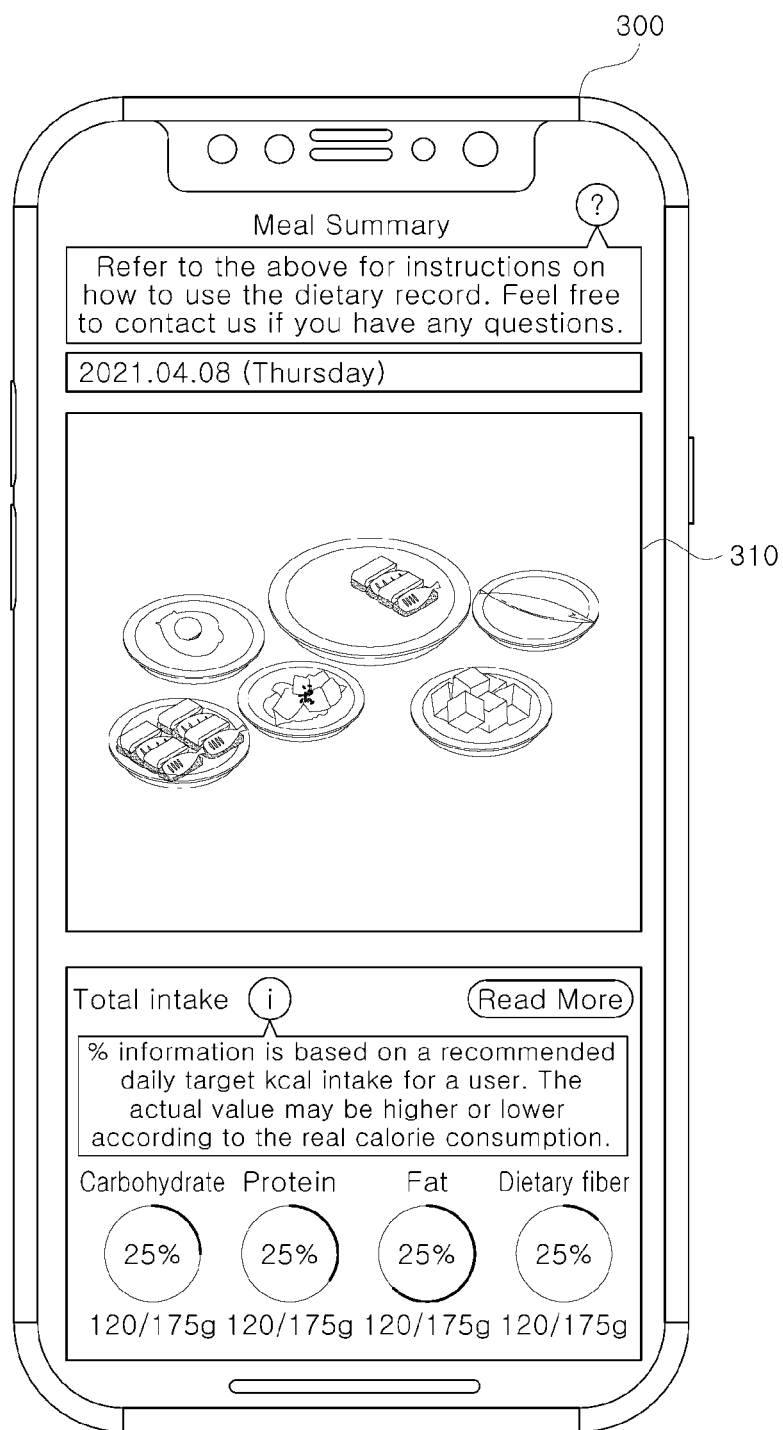
FIG. 17 is a view illustrating an example in which nutritional information generated according to an embodiment of the present disclosure is displayed on a display unit in a user terminal.

FIG. 17 is a view illustrating an example in which nutritional information generated according to an embodiment of the present disclosure is displayed on a display unit in a user terminal.

Referring to FIG. 17, after performing imaging as illustrated in FIGS. 15A to 15D, the user terminal 300 may transmit the captured image to the service providing apparatus 200, and may receive nutritional information analyzed based on the captured image from the service providing apparatus 200.

The nutritional information is displayed by being visualized on the display unit 310 of the user terminal 300, thereby enabling the user to easily confirm the nutritional information.

Meanwhile, the present disclosure performs a preprocessing operation with respect to at least one image to detect at least one food from each image. Hereinafter, an operation of detecting at least one food through at least one image based on FIGS. 18 to 20 will be described in detail.

Figure 18:
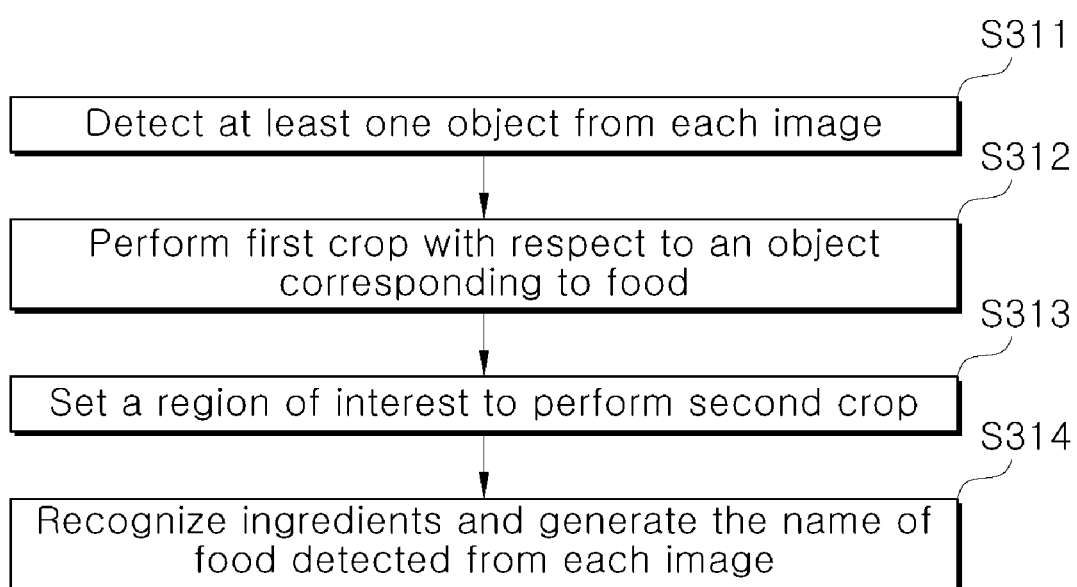
FIG. 18 is a view illustrating an order of operations of detecting at least one food from at least one image obtained using a learning model to provide nutritional information based on image analysis using artificial intelligence according to an embodiment of the present disclosure.

FIG. 18 is a view illustrating an order of operations of detecting at least one food from at least one image obtained using a learning model to provide nutritional information based on image analysis using artificial intelligence according to an embodiment of the present disclosure, and concretizes operation S310 of FIG. 3.

Referring to FIG. 18, in a case in which at least one image is received, the service providing apparatus 200 detects at least one object from each image by inputting at least one image (S311), and generates an image for each food by performing a first crop with respect to an object corresponding to the food in the detected object (S312).

Next, the service providing apparatus 200 sets a region of interest in the image for each food primarily cropped by operation S312 to perform pre-processing by performing a secondary crop (S313). Thereafter, the service providing apparatus 200 generates the name of the food detected from each image by recognizing ingredients from the image for each food secondarily cropped (or preprocessed) (S314). In this instance, operations from S312 to S313 concretize the preprocessing operation for each image in which at least one object is detected by operation S311. That is, the service providing apparatus 200 preprocesses at least one image from which at least one object is detected, and then, recognizes ingredients from each of the preprocessed images to generate names for each food. However, this is just an example, and the preprocessing operation is not limited by the primary crop and the secondary crop, and additional operations may be further performed or the cropping operation may be performed once.

At least one food detected from the at least one image can be confirmed through the generated name of the food.

The service providing apparatus 200 performs mapping with the pre-stored food information in operation S320 using the generated name of the food.

Figure 19:
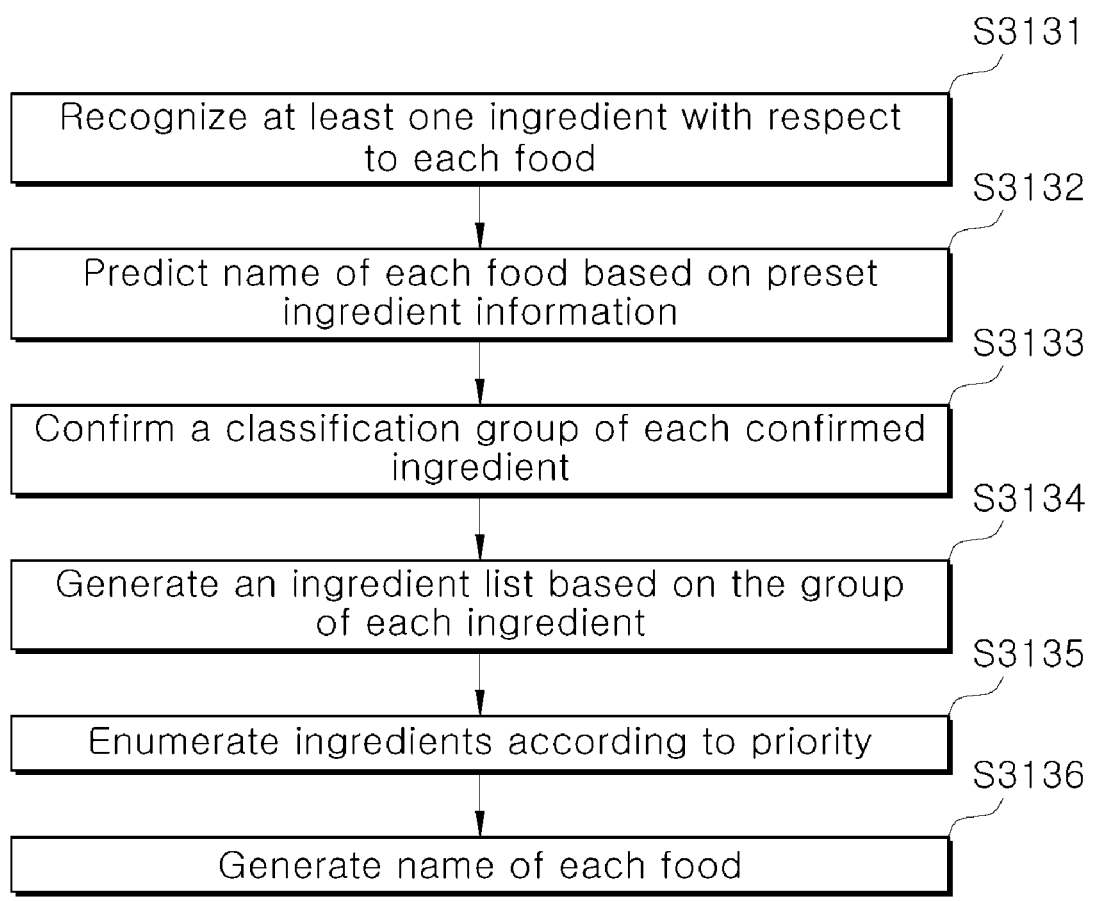
FIG. 19 is a view illustrating an order of operations of processing ingredients recognized when detecting at least one food from at least one image according to an embodiment of the present disclosure.

FIG. 19 is a view illustrating an order of operations of processing ingredients recognized when detecting at least one food from at least one image according to an embodiment of the present disclosure.

Referring to FIG. 19, the service providing apparatus 200 recognizes at least one ingredient for each food from the secondarily cropped image for each food (S3131), and predicts the name of each food based on the recognized ingredient and the pre-stored ingredient information (S3132). Here, the pre-stored ingredient information may include a major ingredient list for each food. However, this is just an example, and the name of each food may be predicted on the basis of big data without using the pre-stored ingredient information.

Next, the service providing apparatus 200 confirms a classification group of each ingredient recognized by operation S3132 (S3133), and generates an ingredient list based on the confirmed group of each ingredient (S3134). When generating an ingredient list, in a case in which ingredients belonging to the same group among the groups of ingredients confirmed by operation of S543 are more than the preset number, the ingredients belonging to the same group may be integrated into an upper group. For instance, in a case in which there are three or more ingredients corresponding to vegetables, such as green onion, paprika, and cucumber, the three ingredients are integrated into 'vegetable', which is an upper group. In a case in which there are three or more ingredients corresponding to fruits, such as apple, orange, and persimmon, the three ingredients are integrated into 'fruit', which is an upper group. In addition, when generating the ingredient list, ingredients which are difficult to recognize may be integrated into an upper group so as to confirm the classification group of the unrecognizable ingredients.

Next, the service providing apparatus 200 may sequentially arrange ingredients on the ingredient list generated by operation S3134 according to a predetermined priority (S3135). In this instance, the priority can be preset by a user or a manager. The priority of the pre-stored ingredient information (including the name of at least one food, and information on basic ingredients) based on preference, importance, calories, nutrients, and the like may be set. For instance, on a preference basis, the priority may be preset in order of ingredient preference of the user, and in this case, the service providing apparatus 200 may previously receive taste information about the user's preferred ingredients and store and manage the taste information as user information. On an importance basis, the priority may be preset in order of importance of ingredients in the relevant food, for instance, in order of major ingredients, minor ingredients, garnish, and the like. On a calorie basis, the priority may be preset in order of calories of ingredients. On a nutrient basis, the priority may be preset in order of having more specific nutrients. That is, the ingredients included in the ingredient list may be enumerated on the basis of the preset priority according to such specific bases.

In addition, when generating the ingredient list, the service providing apparatus 200 may allow the user to utilize only the preset number of ingredients, and allow the user to utilize only ingredients which are not included in the basic ingredients included in the pre-stored ingredient information. However, operation S3135 may be omitted, and is not essential. For instance, in a case in which an object in an image is predicted as Gimbap, if ingredients recognized from the image are steamed rice, pickled radish, and tuna and the basic ingredients of Gimbap confirmed in the pre-stored ingredient information are steamed rice, pickled radish, and tuna, the ingredient list includes only tuna among the recognized ingredients.

Next, the service providing apparatus 200 displays the name of each food predicted by operation S3132 and the ingredient list arranged by operation S3135 together, and generates a food name corresponding to each food (S3136).

On the other hand, the disclosed embodiments may be implemented in the form of a recording medium storing instructions executable by a computer. Instructions may be stored in the form of program code and, when executed by a processor, may generate a program module to perform operation of the disclosed embodiments. The recording medium may be embodied as a computer-readable recording medium.

The computer readable recording medium includes all kinds of recording media in which instructions that can be decrypted by a computer are stored. For example, there may be a read-only memory (ROM), a random access memory (RAM), a magnetic tape, a magnetic disk, a flash memory, an optical data storage device, and the like.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

Advantageous Effects

As described above, the system and the method according to the present disclosure can automatically record and analyze an image including meal information of a user and generate and provide nutritional information according to the analysis result obtained using artificial intelligence, thereby allowing a user to conveniently monitor his or her eating habits in real time.

The advantages of the present disclosure are not limited to the above-mentioned advantages, and other advantages, which are not specifically mentioned herein, will be clearly understood by those skilled in the art from the following description.

The invention claimed is:

1. A system for measuring dish size and providing nutritional information using image recognition and augmented reality based on artificial intelligence, the system comprising:
   at least one imaging device acquiring at least one image including at least one dish or at least one food contained in each dish;
   a service providing apparatus for detecting the at least one dish and the at least one food from the at least one image when the at least one image is received, confirming the name of each detected food on the basis of a learning model, predicting the size of each detected dish, predicting the volume of each detected food using the predicted size of the dish, and generating nutritional information using the predicted volume of each food and pre-stored food information; and
   a user terminal for visualizing and displaying the nutritional information when the nutritional information is received,
   wherein the size of each detected dish is predicted obtained using any one among a first method and a second method, the first method is a method of realizing and using the at least one image in augmented reality, and the second method is a method of detecting and using at least one bounding box from the at least one image.

2. The system according to claim 1, wherein the imaging device includes at least one among a two-dimensional camera, a three-dimensional camera, a time-of-flight (ToF) camera, a light field camera, a stereo camera, an event camera, an infrared camera, a lidar sensor, and an array camera.

3. The system according to claim 2, wherein the at least one imaging device 100 is provided in at least one among a first form in which the imaging device is disposed to the user terminal, a second form in which the imaging device is disposed to the service providing apparatus, and a third form in which the imaging device is arranged and installed in a specific space.

4. The system according to claim 3, wherein in a case in which the first method is used when the size of each detected dish is predicted, the service providing apparatus determines an area of the relevant dish included in the at least one image by realizing the at least one image based on augmented reality, classifies the type of the relevant dish based on the determined area, and confirms the size of the relevant dish corresponding to the type of the relevant dish.

5. The system according to claim 4, wherein when the volume of the detected food is predicted, the service providing apparatus measures an imaging angle by recognizing a bottom surface from at least one image realized on the basis of the augmented reality, and predicts the volume of the relevant food located in the relevant dish based on the measured imaging angle and the size of the predicted dish.

6. The system according to claim 1, wherein in a case in which the first method is used when the size of each detected dish is predicted, the service providing apparatus detects at least one bounding box from the at least one image, detects the relevant dish or the relevant food from each detected bounding box, and confirms the type of the relevant dish and an overlapping rate between the relevant dish and the relevant food to predict the volume of the predicted food.

7. The system according to claim 5, wherein the service providing apparatus calculates weight of each detected food based on the volume of the predicted food using the pre-stored food information to generate nutritional information.

8. The system according to claim 7, wherein the pre-stored food information includes at least one among name information, recipe information, nutritional content information, and basic weight information on at least one food,
   wherein the recipe information includes basic ingredient information including at least one ingredient necessary for cooking each of plural foods, and weight information on each ingredient, and
   wherein the service providing apparatus calculates weight of each detected food based on the recipe information.

9. A method for measuring dish size and providing nutritional information using image recognition and augmented reality based on artificial intelligence, which is performed by an apparatus, the method comprising the operations of:
   classifying and detecting at least one dish and at least one food contained in each dish from at least one image when the at least one image is received;
   predicting the size of each detected dish based on a learning model;
   predicting the volume of each detected food using the predicted size of the dish based on the learning model; and
   generating nutritional information using the predicted volume of each food and pre-stored food information,
   wherein any one among a first method and a second method is used when the size of each detected dish is predicted, the first method is a method of realizing and using the at least one image in augmented reality, and the second method is a method of detecting and using at least one bounding box from the at least one image.

10. The method according to claim 9, wherein in a case in which the first method is used, the operation of predicting the size of each detected dish comprises determining an area of the relevant dish included in the at least one image by realizing the at least one image based on augmented reality, classifying the type of the relevant dish based on the determined area, and confirming the size of the relevant dish corresponding to the type of the relevant dish.

\* \* \* \* \*